United States Patent [19]

Novikov et al.

[11] Patent Number: 4,835,470

[45] Date of Patent: May 30, 1989

[54] MAGNETIZER HAVING A MAIN ELECTROMAGNET AND LEAKAGE FLUX REDUCING AUXILIARY ELECTROMAGNETS FOR MAGNETOGRAPHIC INSPECTION

[75] Inventors: Alexei E. Novikov; Leonid A. Putan, both of Minsk; Valery I. Meerovich; Anatoly N. Semizelnikov, both of Leningrad; Vladimir P. Pokatilov, Moscow, all of U.S.S.R.

[73] Assignee: Belorussky Politekhnitchesky Institute, Minsk, U.S.S.R.

[21] Appl. No.: 18,922

[22] Filed: Feb. 25, 1987

[30] Foreign Application Priority Data

Jul. 2, 1986 [SU] U.S.S.R. ............................ 4077398

[51] Int. Cl.⁴ .................... G01N 27/85; H01F 13/00
[52] U.S. Cl. .................................. 324/213; 324/228; 335/284; 335/304
[58] Field of Search ............... 324/200, 213–216, 324/227, 228, 232, 239, 262; 335/284, 289, 301, 304

[56] References Cited

U.S. PATENT DOCUMENTS

| 2,842,737 | 7/1958 | Zoltan | 324/229 |
| 2,892,150 | 6/1959 | Nettles et al. | 324/220 |
| 3,271,664 | 9/1966 | Mountz et al. | 324/227 |
| 3,430,133 | 2/1969 | Greiner et al. | 324/213 |
| 4,058,762 | 11/1977 | Holt et al. | 324/216 |
| 4,477,776 | 10/1984 | Spierer | 324/232 X |
| 4,490,675 | 12/1984 | Knuettel et al. | 335/301 X |
| 4,594,549 | 6/1986 | Smith et al. | 324/232 |

FOREIGN PATENT DOCUMENTS

| 214869 | 5/1968 | U.S.S.R. | |
| 418786 | 8/1974 | U.S.S.R. | |
| 1196750 | 12/1985 | U.S.S.R. | 324/228 |

Primary Examiner—Gerard R. Strecker
Attorney, Agent, or Firm—Lilling & Greenspan

[57] ABSTRACT

A magnetizer for magnetographic inspection of articles comprises a main electromagnet, an auxiliary electromagnet, and a power supply unit for the windings of the electromagnets. The auxiliary electromagnet is offset with respect to the central zone of the magnetic field established by the main electromagnet, in a direction perpendicular to that of the magnetic lines of force of the main electromagnet, and is mounted for changing its position.

6 Claims, 4 Drawing Sheets

Switch — Power supply unit — Multifrequency pulse generator

MAGNETIZER HAVING A MAIN ELECTROMAGNET AND LEAKAGE FLUX REDUCING AUXILIARY ELECTROMAGNETS FOR MAGNETOGRAPHIC INSPECTION

BACKGROUND OF THE INVENTION

1. Field of the Invention

The present invention generally relates to measurement technology and more specifically to magnetizers for magnetic inspection of articles and is aimed at magnetic recording of flaw margins in the course of magnetic flaw detection, e.g., in the case of quality inspection of intricately shaped ferromagnetic components or of some individual surface areas thereof.

2. Description of the Prior Art

One prior art magnetizer is known to comprise a number of series-connected electromagnets. Such a device enables magnetization of a rather long section of a weld seam on which magnetic tape is applied, but fails to establish a homogeneous magnetic field within the zone of the welded joint. Besides, magnetic tape induces additional distortions developed when magnetograms are decoded, this being due to the fact that when there is a variable profile of the surface under inspection, e.g., in the case of a weld reinforcement, the magnetizer fails to provide a uniform magnetic flux within the zone of the magnetic tape. Moreover, it is a difficult task with the known magnetizer to attain magnetic tape operation on the linear portion of its B-H curve (cf. USSR Inventor's Certificate No. 214,869, Class 42 K 46/03 published in 1968).

Known in the present state of the art is another magnetizer for magnetographic inspection of articles, comprising a main electromagnet, an auxiliary electromagnet (of lower power as compared with the main electromagnet) interposed between the poles of the main electromagnet in the central zone of the magnetic field thereof in such a manner that the intrinsic magnetic field of the auxiliary electromagnet is capable of interacting with the field established by the main electromagnet, and a power supply unit for the windings of the electromagnets (cf. USSR Inventor's Certificate No. 418,786, Class G OI N 27/82 published in 1974).

The auxiliary electromagnet provides for establishing of an additional magnetic flux in the zone of the article being magnetized with the main electromagnet, the additional magnetic flux correcting the component of the main magnetic field in this zone, which is the case with, e.g., weld inspection when the additional magnetic flux is to correct the main electromagnet magnetic flux component within the weld zone, said component being closed through the weld bead.

However, there exist a great number of articles (e.g., intricately shaped heavy-weight sturdy items such as diesel-engine framework, various beds and frames, butt-joints of pipes featuring different wall thickness, and the like), wherein apart from the presence of a weld seam within the zone under inspection, there are also such specific features as an intricate profile of the article itself and variable thickness across the zone under inspection. This leads to leaks of the magnetic flux into the heavy cross-section zone of the article in the course of magnetographic inspection, as well as to inhomogeneous magnetic flux, adversely affected sensitivity of the inspection method and hence makes it impossible to provide magnetic tape operation on the linear portion of its characteristic (B-H) curve. All this results in failure to detect some flaws, e.g., such hard-to-reveal ones as dissimilarly oriented defects, or introduces errors in determination of the size of a defect.

SUMMARY OF THE INVENTION

It is an object of the invention to provide higher homogeneity of the magnetic flux within the zone of inspection of intricately shaped articles.

It is another object of the invention to reduce errors introduced into the flaw detection process due to non-linearity of magnetic tape.

The essence of the invention resides in the fact that in a magnetizer for magnetographic inspection of articles, comprising a main electromagnet, an auxiliary electromagnet interposed between the poles of the main electromagnet in such a manner that its field is capable of interacting with the field of the main electromagnet, and a power supply unit for the windings of the electromagnets, according to the invention, the auxiliary electromagnet is offset with respect to the central zone of the main electromagnet.

It is expedient that the magnetizer aimed at inspecting articles whose cross-section increases symmetrically to either side of the inspection zone be provided with a second auxiliary electromagnet which is connected to the power supply unit, is similar to the first auxiliary electromagnet and is arranged symmetrically to the latter with respect to the central zone of the magnetic field established by the main electromagnet.

It is desirable that the auxiliary electromagnets be mounted for movement to make it possible to either move them apart or bring them together.

To make possible magnetographic inspection of tubular articles, the magnetizer advantageously includes a third auxiliary electromagnetic and a fourth auxiliary electromagnet, the windings of both electromagnets being connected to the power supply unit, said electromagnets being situated outside the interpolar space of the main electromagnet and each of said electromagnets being arranged against one of the poles of the main electromagnets so that the magnetic lines of force of the main electromagnet and of the third and fourth auxiliary electromagnets are parallel to one another, and the fields of the third and fourth auxiliary electromagnets are capable of interacting with the field of the main electromagnet.

To attain higher reliability and economy of magnetographic inspection, the magnetizer is advantageously provided with a multifrequency pulse generator connected in between the output of the power supply unit and the windings of the first and second auxiliary electromagnets.

The magnetizer for magnetographic inspection of articles made according to the invention enables one to carry out high-sensitivity defectoscopic examination of intricately shaped articles due to the provision of uniform magnetization of the article zone under inspection regardless of the presence of variable-thickness portions therein.

In addition, the magnetizer according to the invention makes it possible to perform magnetic recording of defects or flaws on the linear portion of the magnetic tape B-H curve under such complicated conditions as mentioned above. This in turn facilitates subsequent processing of the flaw detection results, thereby adding to the quality of inspection.

BRIEF DESCRIPTION OF THE DRAWINGS

The invention will now be described by way of specific embodiments thereof with reference to the accompanying drawings, wherein.

DESCRIPTION OF THE PREFERRED EMBODIMENTS

Figure 1:
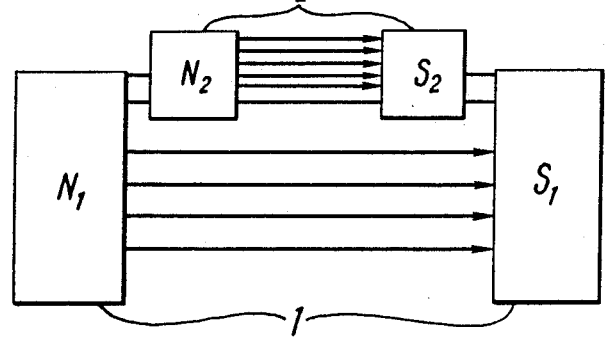
FIG. 1 is a schematic plan view of an embodiment of the magnetizer for magnetographic inspection of articles featuring a one-sided increase in the cross-sectional area of the zone under inspection.

The magnetizer for magnetographic inspection of articles, according to the present invention, comprises a main electromagnet 1 (FIG. 1) and an auxiliary electromagnet 2 interposed between the poles $N_1$–$S_1$ of the main electromagnet 2. As can be seen from FIG. 1 the auxiliary electromagnet 2 is somewhat offset with respect to the central zone of the magnetic field established by the main electromagnet 1 in a direction perpendicular to the direction of the magnetic lines of forces of the electromagnet 1 in such a manner that the magnetic field established by the auxiliary electromagnet 2 can interact with the magnetic field produced by the main electromagnet 1. FIG. 1 represents the case where the fields of the electromagnets 1 and 2 are parallel, run in the same direction and interact with each other. Such a combination of the two electromagnets 1, 2 is adapted for inspection of articles featuring a variable cross-sectional area with the latter increasing unilaterally, i.e., towards the electromagnet 2. In this case the auxiliary electromagnet 2 is installed in the initial portion of the increasing-area section. No means for altering the position of the electromagnet 2 is represented in FIG. 1. A worm gearing provided with guides, a screw-and-nut drive, and the like may be used for this purpose. By the "central" zone of the magnetic field of the electromagnet 1 is meant the area of the interpolar space where the magnetic field is homogeneous. The power supply unit for the windings of the electromagnets 1 and 2 is omitted in FIG. 1.

Figure 4:
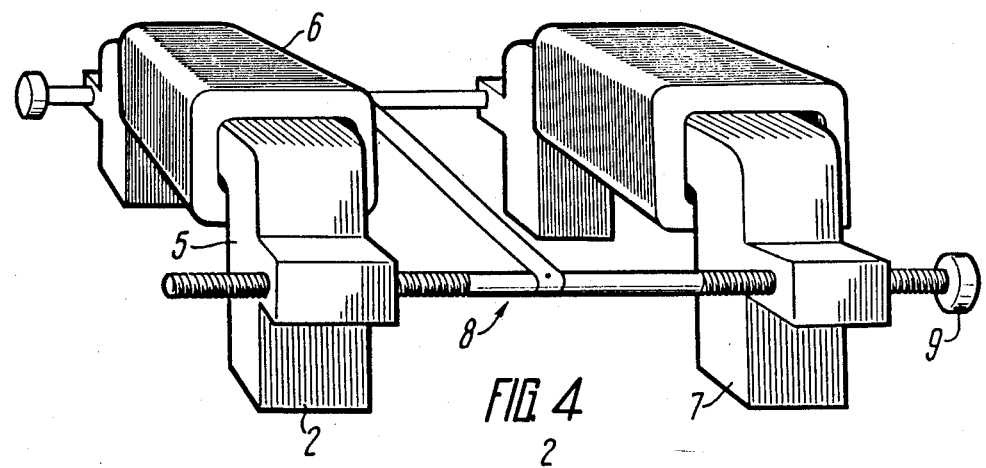
FIG. 4 is a scaled-up perspective view of auxiliary electromagnets taken along the line A in FIG. 2.
Figure 2:
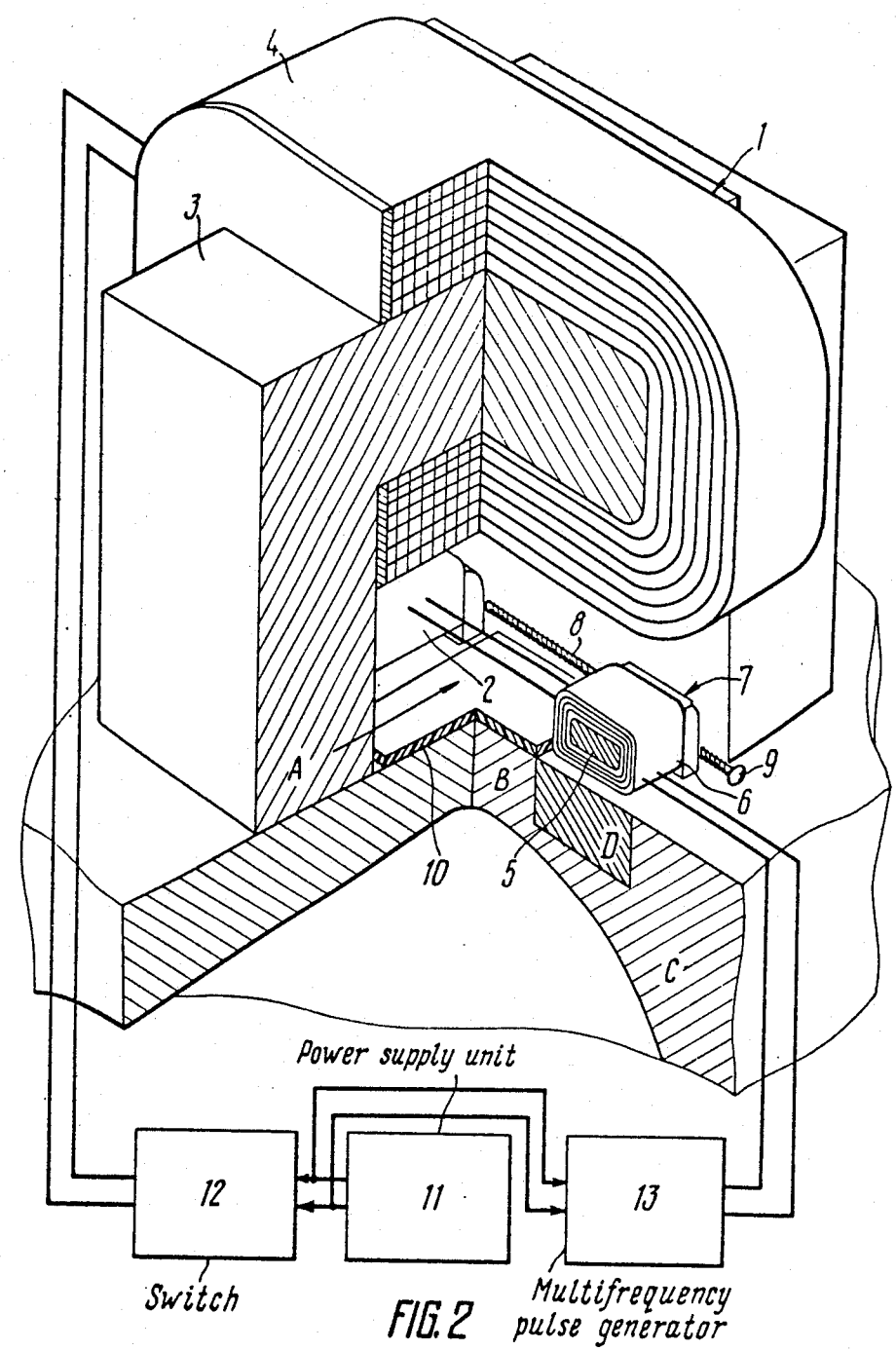
FIG. 2 is a general perspective view of an embodiment of the magnetizer for magnetographic inspection of articles partially in cross-section, featuring a double-sided symmetrical increase in the cross-sectional area of the zone under inspection.
Figure 3:
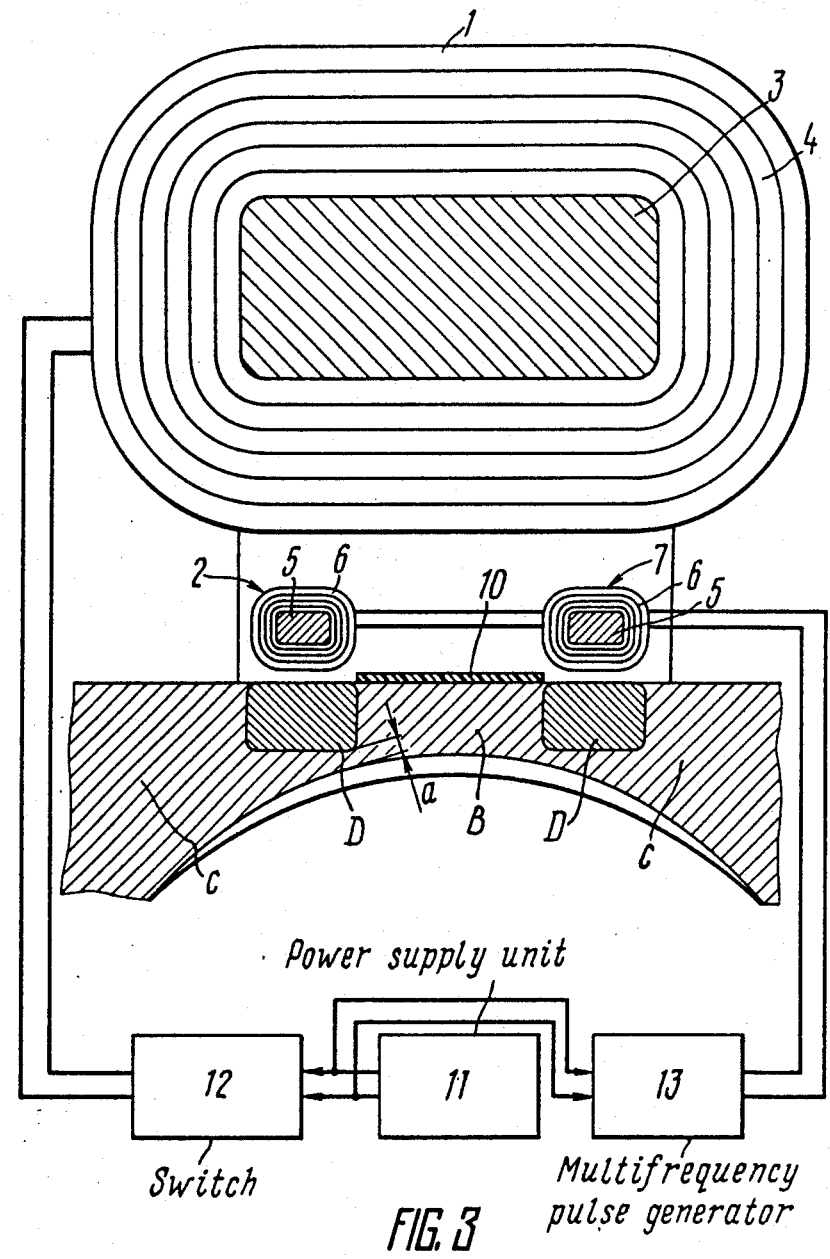
FIG. 3 is a cross-sectional view of FIG. 2.

FIGS. 2, 3 and 4 illustrate an embodiment of the magnetizer for magnetographic inspection of articles featuring their thickness increasing symmetrically from the central portion towards the periphery. The embodiment of the magnetizer includes, apart from the main electromagnet 1 consisting of a magnetic core 3 and a winding 4, and the auxiliary electromagnet 2 consisting of a magnetic core 5 and a winding 6, one more auxiliary electromagnet 7 which is similar to the auxiliary electromagnet 2 and consists also of a magnetic core 5 and a winding 6.

The auxiliary electromagnets 2 and 7 are arranged symmetrically with respect to the central zone of the interpolar space of the main electromagnet 1 with a possibility of being moved either apart or together, for which a traversing means 8 is provided. The traversing means 8 may be, e.g., roller guideways, a worm gearing, and the like. FIG. 4 illustrates one possible embodiment of the traversing means 8 for moving the auxiliary electromagnets 2 and 7 in the form of a screw-and-nut drive. Rotation of the screw 9 by its head beings the electromagnets 2 and 7 either together or apart, i.e., moves them in a direction perpendicular to the direction of the magnetic lines of force of the main electromagnet 1. A magnetic tape 10 (FIGS. 2, 3) adheres tightly to the surface of the article under inspection and passes through the central zone of the interpolar space of the main electromagnet 1.

To supply the windings 6 of the electromagnets 2 and 7 with direct current the magnetizer is provided with direct current the magnetizer is provided with a power supply unit 11 which is essentially a source of rectified voltage, and with a switch 12.

Besides, a multifrequency pulse generator 13 is provided connected to the auxiliary electromagnets 2 and 7, said generator being connected in between the output of the power supply unit 11 and the windings 6 of the auxiliary electromagnets 2 and 7. The multifrequency pulse generator 13 may be a thyristor rectifier provided with an input timing relay and a pulse sharper, or use may be made of an alternating-current voltage source.

Figure 5:
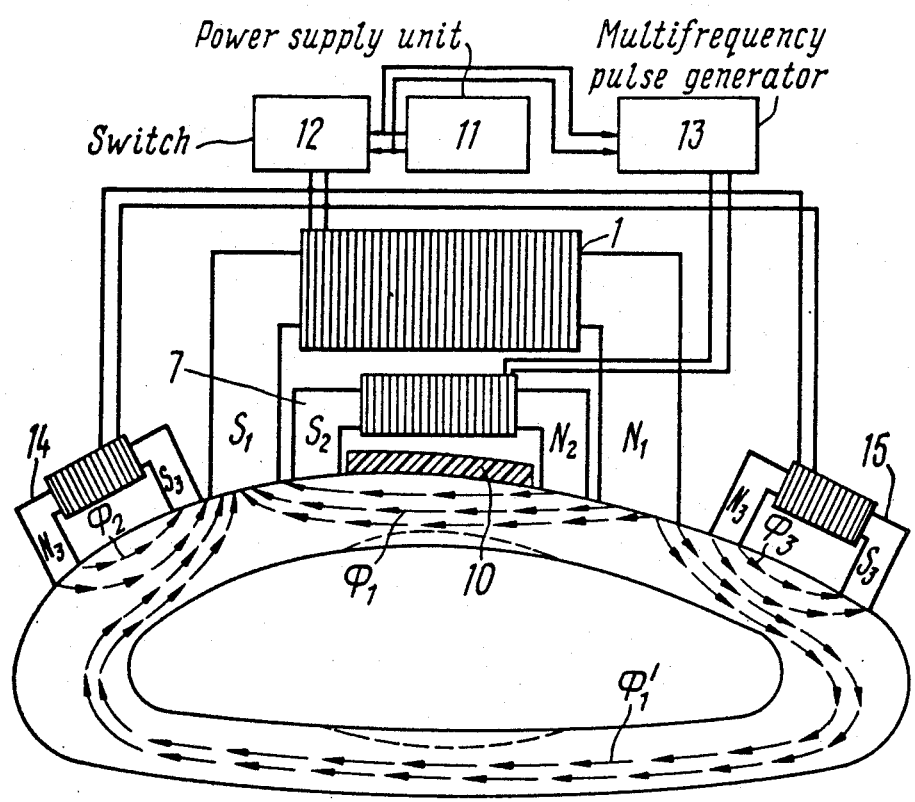
FIG. 5 is a cross-sectional view of an embodiment of the magnetizer for magnetographic inspection of articles tubular in shape.
Figure 6:
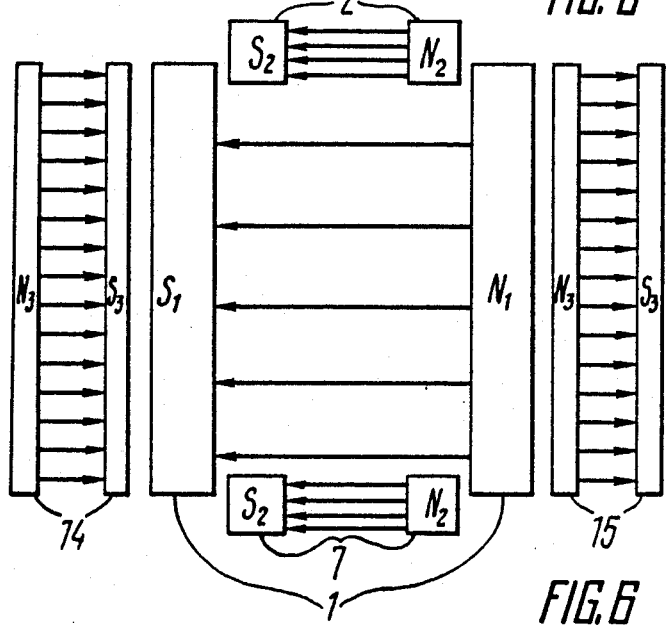
FIG. 6 is a schematic plan view of the magnetic system of the magnetizer shown in FIG. 5.

FIGS. 5 and 6 illustrate an embodiment of the magnetizer for defectoscopic examination of tubular-shaped articles, such as variable cross-section curved pipes or tubes.

Unlike the magnetizer embodiments illustrated in FIGS. 1 and 2, the embodiment represented in FIGS. 5 and 6 incorporates a third auxiliary electromagnet 14 and a fourth auxiliary electromagnet 15 whose windings are connected to the power supply unit 11 through a rheostatic switch 12. The auxiliary electromagnets 14 and 15 are arranged as follows: one against the pole $N_1$ of the main electromagnet 1, the other opposite to the pole $S_1$ of the main electromagnet 1 in such a manner that the magnetic lines of force of the main electromagnet 1 and of the auxiliary electromagnets 14 and 15 are parallel to one another and the fields of the auxiliary electromagnets 14 and 15 are capable of interacting with the field of the main electromagnet 1. For the sake of clarity FIG. 5 illustrates the following magnetic fluxes: $\Phi_1$—the main electromagnet flux which is closed through the zone under inspection, and $\Phi_1'$——the flux of the main electromagnet 1 which is branched off to the nonmagnetizable portion of a tubular-shaped article, as well as fluxes $\Phi_2$ and $\Phi_3$ of the respective auxiliary electromagnets 14 and 15, both of them interacting with the flux $\Phi_1'$. The auxiliary electromagnets 2 and 7 in the embodiment under consideration are also connected to the multi-frequency pulse generator 13 which is likewise connected between the output of the power supply unit 11 and the windings 6 of the auxiliary electromagnets 2 and 7.

The magnetizer for magnetographic inspection, according to the invention, operates as follows.

To carry out magnetographic inspection of an article, magnetic flux is induced therein with the aid of the magnetizer disclosed in this invention, with the result that the lines of force of the magnetic field are arranged predominantly in the same direction. Should the article under examination exhibit any flaw, such as crack, blowhole, blister, etc., magnetization of the article under inspection will result in a magnetic stray field arising from the flaw at the place of its location, i.e., above the flaw on the surface of the article. Otherwise speaking, part of the magnetic lines of force emerge to the surface of the article's zone under inspection, whereupon this stray field is recorded on the magnetic tape in contact with the surface of the zone under examination. To read out, decode and interpret the magnetic tape records use may be made of a conventional reproducing unit of a magnetic flaw detector provided with sensors capable of responding to the magnetic flux variations recorded on the magnetic tape, said reproducing unit being also capable of representing the flaw arrangement pattern practically on any scale as an acceptance document.

To subject an article to magnaflux inspection, the magnetizer of the invention and the magnetic tape 10 (FIGS. 1, 2, 3, 4) are placed on the surface of the article being inspected and the power supply unit 11 is connected to power mains. Then the main electromagnet 1 and the auxiliary electromagnets 2 and 7 are set in the initial position depending on the type of magnetic tape, i.e., its magnetic characteristics (B-H curve) and the cross-sectional configuration of the article within the zone under inspection. The main electromagnet 1 is placed on the surface of the article's zone being inspected (which is as a rule the thinnest portion of the article's cross-section). When the cross-sectional area of the article under inspection increases unilaterally use is made of the magnetizer with one auxiliary electromagnet 2 which is disposed in the interpolar space of the electromagnet 1 and is somewhat offset with respect to the central zone of the magnetic field established by the electromagnet 1 in the initial portion of the increasing-section of the article. When the cross-sectional area of the article under examination increases symmetrically on both sides use is made of the magnetizer with two auxiliary electromagnets 2 and 7 which are situated in the interpolar space of the electromagnet 1 and are offset in the opposite direction from the central zone of the magnetic field of the electromagnet 1 at the origin of either of the zones of increasing article's cross-sectional area.

In what follows the operation of the magnetizer embodiment illustrated in FIGS. 2, 3 and 4 and covering also the embodiment thereof shown in FIG. 1 will be discussed in more detail.

The winding 4 of the electromagnet 1 is energized by means of the rheostatic switch 12, whereby the article's area under inspection and the magnetic tape 10 are magnetized. As a result, part of the magnetic flow is closed through a thin portion 'B' of the zone under inspection, while another portion of the flux is branched off to the thickened portions 'C' of the article. Once the quasi-stationary operating conditions have set in, within the zone under inspection, the pulse generator 13 (connected to the windings 6 of the auxiliary electromagnets 2, 7) is energized after a 2 or 3-second delay obtained due to a delay element, such as a timing relay provided at the input of the pulse generator 13. As a result, additional magnetic fluxes of the electromagnets 2 and 7 arise in the portions 'D' of the article's zone under inspection, thus bringing about magnetic saturation of the ferromagnetic material of the article under examination on its sections 'D'. This in turn prevents the main magnetic flux from leaking out to the heavier-thickness portions 'C' of the metallic article. Thus, the maximum sensitivity behaviour of the magnetizer is attained. The shape of the current pulses feeding the windings 6 of the auxiliary electromagnets are so selected as to attain saturation magnetization of the sections 'D' (i.e., that incorporating the maximum low-frequency component). By varying the oscillation frequency of the pulse generator 13 one can attain a required thickness of the saturated sections 'D' and a desired amount of the air gap 'a' for part of the magnetic flux of the electromagnet 1 to escape.

A similar result can be obtained by rotating the head of the screw 9, thus mutually displacing the auxiliary electromagnets 2 and 7, i.e., either bringing them together or apart in a direction perpendicular to the magnetic lines of force of the electromagnet 1 at a definite preset magnetization depth which depends on the oscillation frequency of the generator 13 or the current pulse shape.

Application of any of the aforementioned techniques or a combination thereof in flaw inspection of variable-thickness articles makes it possible to equalize the magnetic field induction values within the zone under inspection and adjust the proportion of magnetic flux leaks into the thickened portios 'C', thus enabling the magnetic tape 10 to operate on the linear portion of its magnetic characteristics (B-H curve).

It is worth noting that with the use of the magnetizer according to the invention, there is no need for the entire article to magnetize to a preset induction value, such as its thickened portions inclusive, particularly since it is not at all times attainable from a technical standpoint (in some cases there exist some dimensional limitations, as well as restrictions as to access to the inspection zone). It is thus enough to magnetize to the saturation level the section 'B' in the boundary zone of transition to a heavier cross-section. This makes it possible to render the flaw detection process more sensitive and to attain a higher economy of the magnetizer itself.

In the case of magnetic flaw detection applied to tubular-shaped articles use is made of the magnetizer embodiment shown in FIGS. 5, 6.

The windings of the main electromagnet 1 and of the auxiliary electromagnets 14 and 15 are energized by means of the rheostatic switch 12. As a result, there are induced in the article under examination the magnetic fluxes $\Phi_1$ and $\Phi_1'$ of the electromagnet 1 and the fluxes $\Phi_2$ and $\Phi_3$ of the respective electromagnets 14 and 15. Once the quasi-stationary operating conditions have set in, the multifrequency pulse generator 13 (connected to the windings 6 of the auxiliary electromagnets 2 and 7) is energized. The auxiliary electromagnets 14 and 15 are so arranged that their magnetic fluxes $\Phi_2$ and $\Phi_3$ are co-current with the leakage flux $\Phi_1'$ of the main electromagnet 1. The magnetic fluxes $\Phi_2$, $\Phi_3$, while interacting with the magnetic leakage flux $\Phi_1'$, adjust its value until its complete restriction, which renders it possible to vary the ratio between the fluxes $\Phi_1$ and $\Phi_1'$, thus providing a required magnetic induction value in the inspection zone of the article.

To attain higher effectiveness of the auxiliary electromagnets 14 and 15 their poles $N_3$-$S_3$ are situated in close vicinity to the poles $N_1$-$S_1$ of the main electromagnet 1 as shown in FIGS. 5 and 6.

In the magnetizer embodiment considered above the auxiliary electromagnets 2 and 7 perform the same function as in the embodiment represented in FIGS. 2, 3 and 4 in the case of an increasing article's cross-sectional area in a direction perpendicular to the direction of the magnetic lines of force of the main electromagnet 1 and operate in the same manner. The electromagnets are energized after the quasi-stationary operating conditions have set in within the inspection zone. Whenever the article's section in the aforementioned direction remain invariable, the auxiliary electromagnets 2 and 7 perform the function of equalizing the induction values, compensating for magnetic flux leakage into the article's zone adjacent to the boundaries of the interpolar space of the main electromagnet 1. As a matter of fact, this prevents part of the magnetic lines of force of the electromagnet 1 from spreading or 'flowing over' beyond the edges of the electromagnet 1 in such a simplified case (i.e., when the inspection zone features a constant-thickness cross-sectional area).

Once the magnetization process has been applied to said zone, magnetization is repeated in the same sequence of steps on a next section of the article under inspection after having transferred the magnetizer to said section.

It should be understood that this invention is by no means limited to the specific and preferred embodiment thereof as disclosed herein by way of example and may have many modifications not departing from the scope and spirit as defined in the claims that follow.

What is claimed is:

1. A magnetizer for magnetographic inspection of articles, comprising:
   a main two-pole electromagnet having a U-shaped core;
   an electric winding provided on said core;
   first and second poles of said two-pole electromagnet, each having a working surface intended for cooperation with the surface of said article being inspected by mounting it on said surface, said cooperation permitting the passage of a magnetic flux produced by said electric winding from the working surface of said first pole toward the working surface of said second pole in the material of said article being inspected, and an interpolar space lying in a region between said first and second poles of said U-shaped core, said interpolar space including a centralzone in which the magnetic field produced by said electric winding is substantially uniform;
   a first auxiliary two-pole electromagnet having a U-shaped core and an electric winding provided on said core;
   poles of said core of the auxiliary electromagnet, each having a working surface intended for cooperation with the surface of the article being inspected, said first auxiliary electromagnet being located in said interpolar space of the main electromagnet so that said working surfaces of the poles of the auxiliary electromagnet are located on said surface of said article between said working surfaces of the poles of the main electromagnetic, said first auxiliary electromagnet being offset relative to and extending at least partially beyond said central zone in a direction normal to the direction of the lines of force of said magnetic field produced by said main electromagnet and so that the lines of force of said magnetic field of said main electromagnet and the magnetic field produced by said electromagnetic winding of the auxiliary electromagnet are parallel and said magnetic fields being capable of interacting with each other for controllably reducing the leakage of said magnetic flux of the main electromagnet through the material of the article being inspected beyond said interpolar space, and
   a power supply unit for said electric windings of the main and auxiliary electromagnets.

2. A magnetizer as claimed in claim 1, comprising:
   a second auxiliary two-pole electromagnet having a U-shaped core, an electric winding provided on said core, and first and second poles, each having a working surface, intended for cooperation with said surface of the article being inspected, said electric winding of the second auxiliary electromagnet being electrically coupled with said power supply unit, and
   said second auxiliary electromagnet being located symmetrically relative to the first auxiliary electromagnet with respect to said central zone of said interpolar space of the main electromagnet.

3. A magnetizer as claimed in claim 2, which comprises means for altering the distance between said first and second auxiliary electromagnets so that they can move toward or away from each other.

4. A magnetizer as claimed in claim 3 wherein said means for altering the distance between said auxiliary electromagnets is a screw pair, comprising:
   a screw of said screw pair positioned so that its axis is normal to the direction of the lines of force of said magnetic field of the main electromagnet, and having first and second ends;
   a helical thread on said first end;
   a helical thread on said second end opposite to said helical thread on said first end;
   a first nut of said screw pair provided in said first auxiliary electromagnet, on said first end;
   a second nut of said screw pair, provided in said second auxiliary electromagnet, on said second end, and
   means for rotating said screw about its said axis.

5. A magnetizer as claimed in claim 2 for magnetographic inspection of articles of tubular cross-sectional area, comprising:
   a third auxiliary two-pole electromagnet having a U-shaped core with two poles, each having a working surface intended for cooperation with said surface of the article being inspected;
   an electric winding provided on said core of the third electromagnet and electrically coupled with said power supply unit;
   said third auxiliary electromagnet being located beyond said interpolar space opposite to one of said poles of the main electromagnet so that the working surfaces of the poles of the third auxiliary electromagnet and the main electromagnet are adapted to be positioned on the outer curved surface of said article being inspected;
   a fourth auxiliary two-pole electromagnet having a U-shaped core with two poles each having a working surface intended for cooperation with said surface of the article being inspected;
   an electric winding provided on said core of the fourth electromagnet and coupled electrically with said power supply unit;
   said fourth auxiliary electromagnet being located beyond said interpolar space opposite to the other said pole of the main electromagnet so that the working surfaces of the poles of the fourth auxiliary electromagnet and the main electromagnet are adapted to be positioned on the outer curved surface of said article being inspected, and
   said third and fourth auxiliary electromagnets being so positioned relative to the main electromagnet that the lines of force of the magnetic fields of said three electromagnets are substantially parallel and the magnetic fields of the third and fourth auxiliary electromagnets are capable of interacting with said magnetic field of the main electromagnet to prevent leakage of said magnetic flux of the main electromagnetic through the material of said article being inspected.

6. A magnetizer as claimed in claim 5, further comprising a multifrequency pulse generator connected between said power supply unit and said windings of said auxiliary electromagnets.

* * * * *